United States Patent [19]
Ullah

[11] Patent Number: 6,040,299
[45] Date of Patent: Mar. 21, 2000

[54] COLD STORAGE STABILIZED ORGANOPHOSPHORUS INSECTICIDE FORMULATION AND METHOD OF MAKING SAME

[75] Inventor: Hamid Ullah, Hahira, Ga.

[73] Assignee: Griffin LLC, Valdosta, Ga.

[21] Appl. No.: 09/177,851

[22] Filed: Oct. 23, 1998

[51] Int. Cl.[7] .............................. A01N 57/00; A01N 57/26
[52] U.S. Cl. ................................. 514/75; 514/82; 514/86; 514/87; 514/89; 514/129; 514/132; 514/137
[58] Field of Search ................................. 424/200; 514/75, 514/89, 86, 87, 82, 129, 132, 137

[56] References Cited

U.S. PATENT DOCUMENTS

| | | | |
|---|---|---|---|
| 4,380,537 | 4/1983 | Monroe | 424/200 |
| 5,140,019 | 8/1992 | Wada et al. | 514/89 |
| 5,165,934 | 11/1992 | Wada et al. | 424/409 |
| 5,260,312 | 11/1993 | Wada et al. | 514/342 |

*Primary Examiner*—Jose' G. Dees
*Assistant Examiner*—Alton Pryor
*Attorney, Agent, or Firm*—Jones & Askew LLP

[57] ABSTRACT

There is disclosed a cold storage stabilized organophosphorus insecticide formulation. The formulation comprises a solid carrier and between approximately 2% and 40% by weight of the ultimate formulation of a nominally solid organophosphorus insecticide and between approximately 0.5% and 10% by weight of the ultimate formulation of a stabilizer compound selected from cyclohexanone and N-methylpyrrolidone. A method of making the cold storage stabilized organophosphorus insecticide formulation is also disclosed.

29 Claims, No Drawings

COLD STORAGE STABILIZED ORGANOPHOSPHORUS INSECTICIDE FORMULATION AND METHOD OF MAKING SAME

FIELD OF INVENTION

The present invention relates generally to insecticides, and, more specifically, to cold storage stabilized organophosphorus insecticide formulations. The present invention also relates to a method of making cold storage stabilized organophosphorus insecticide formulations.

BACKGROUND OF THE INVENTION

Organophosphorus compounds are well known in the art as agricultural insecticides. Organophosphorus compounds have been formulated both as liquid and as solid products. The solid formulations have been sold as both powders and granules; however, the granular form is most commonly used today.

Organophosphorus insecticides are relatively unstable molecules and tend to decompose readily, particularly when exposed to high or low pH. Furthermore, organophosphorus compounds will undergo hydrolysis in the presence of water. Thus, it is known in the prior art that the chemical stability of solid formulations of organophosphorus insecticides can be enhanced by the addition of certain materials that reduce the rate of chemical degradation of the active ingredient.

U.S. Pat. Nos. 4,380,537; 5,140,019; 5,165,934 and 5,260,312 all disclose organophosphorus insecticides on solid carriers, such as clays. Specifically, U.S. Pat. No. 4,380,537 discloses an insecticide formulation containing an organophosphorus insecticide, such as chlorpyrifos, on a clay carrier, such as montmorillonite or attapulgite, and as a stabilizer for the insecticide between 0.5% and 10% by weight of a lactone. Other stabilizers of organophosphorus insecticides known in the prior art include polyethyleneglycol and polypropyleneglycol. W. Kelley et al., "Use of Deactivators in Granular Clay Formulations," discloses the use of ethanolamine, ethyleneglycol (and dimers thereof), propyleneglycol (and dimers thereof), and urea as deactivators for formulations of pesticides on clay-based granules. However, the stabilized insecticidal formulations of the prior art have not always been satisfactory.

A formulation of 15% by weight chlorpyrifos on a granular clay carrier and 4.5% by weight of dipropyleneglycol as a stabilizer is unsatisfactory for agricultural use upon cold storage. After storage at relatively cold temperatures, the granules will agglomerate and form hard lumps that make the formulation unsuitable for agricultural application using conventional equipment. Heretofore, it has not been known how to stabilize granular formulations of organophosphorus insecticides against agglomeration or clumping that result from cold storage.

Therefore, a need exists for an improved cold storage stabilized organophosphorus insecticide formulation.

SUMMARY OF THE INVENTION

The present invention satisfies the above-described needs by providing an improved insecticidal formulation. The insecticidal formulation of the present invention comprises a solid carrier to which has been applied between approximately 2% and 40% by weight of the ultimate formulation of a nominally solid organophosphorus insecticide and between approximately 0.5% and 10% by weight of the ultimate formulation of a stabilizer compound selected from cyclohexanone and N-methylpyrrolidone.

Another embodiment of the present invention comprises a method of making an insecticidal formulation. The method comprises mixing with a solid carrier between approximately 2% and 40% by weight of the ultimate formulation of a nominally solid organophosphorus insecticide in a liquid state and between approximately 0.5% and 10% by weight of a stabilizer compound selected from cyclohexanone and N-methylpyrrolidone.

Another embodiment of the present invention comprises a method of making an insecticidal formulation comprising mixing with a solid carrier at a temperature of between approximately 30° and 200° C. between approximately 2% and 40% by weight of the ultimate formulation of a nominally solid organophosphorus insecticide in a liquid state and between approximately 0.5% and 10% by weight of the ultimate formulation of a stabilizer compound selected from cyclohexanone and N-methylpyrrolidone.

Accordingly, it is an object of the present invention to provide an improved insecticidal formulation and an improved method for making an insecticidal formulation.

Another object of the present invention is to provide an insecticidal formulation that has improved cold storage stability.

Yet another object of the present invention is to provide an insecticidal formulation that is flowable and resists agglomeration or clump formation upon cold storage.

These and other objects, features and advantages of the present invention will become apparent after a review of the following detailed description of the disclosed embodiments and the appended claims.

DETAILED DESCRIPTION OF THE DISCLOSED EMBODIMENTS

The present invention provides a cold storage stabilized organophosphorus insecticide formulation and a method of making a cold storage stabilized organophosphorus insecticide formulation. The organophosphorus insecticide formulation comprises a solid carrier to which has been applied a nominally solid organophosphorus insecticide and a stabilizer compound. In accordance with the present invention, the nominally solid organophosphorus insecticide comprises between approximately 2% and 40% by weight of the ultimate formulation; preferably, between approximately 10% and 20% by weight of the ultimate formulation; especially, approximately 15% by weight of the ultimate formulation. The stabilizer compound comprises between approximately 0.5% and 10% by weight of the ultimate formulation; preferably, between approximately 2% and 5% by weight of the ultimate formulation. In relative terms, the ratio of nominally solid organophosphorus insecticide to stabilizer compound is between approximately 80:1 and 4:1 by weight.

As used herein the term "nominally solid organophosphorus insecticide" designates and means those organophosphorus insecticides that solidify within the temperature range at which the formulation would normally be applied and/or stored. Generally, those temperatures at which the formulation would normally be applied and/or stored will be as low as 0° F. and as high as 110° F. Therefore, the present invention is applicable to those organophosphorus insecticides that will solidify at temperatures between approximately 0° F. and 110° F. (−17.8° and 43° C.).

The nature of the nominally solid organophosphorus insecticide is not critical to the present invention. The only qualification is that it may solidify at temperatures at which the formulation would normally be applied and/or stored as defined above. The present invention is applicable to nominally solid organophosphorus insecticides in general. Organophosphorus insecticides useful in the present invention that are clearly solids at temperatures at which the formulation would normally be applied and/or stored include those compounds shown in Table 1 below:

TABLE 1

| Common Name | Chemical Name |
| --- | --- |
| Acephate | O,S-dimethyl acetylphosphoramidothioate |
| Bromophos | O-(4-bromo-2,5-dichlorophenyl) O,O-dimethyl phosphorothioate |
| Chlorpyrifos | O,O-diethyl O-(3,5,6-trichloro-2-pyridyl) phosphorothioate |
| Disulfoton | O,O-diethyl-S-ethylmercaptoethyl dithiophosphate |
| EPN | O-ethyl O-p-nitrophenylthiobenzene phosphonate |
| Fenamiphos | Ethyl 4-(methylthio)-m-tolyl isopropylphosphoramidate |
| Fenchlorophos | dimethyltrichlorophenylthiophosphate |
| Quinalphos | O,O-diethyl O-2-quinoxalinyl phosphorothioate |
| Trichlorfon | O,O-dimethyl-1-hydroxy-2,2,2-trichloroethylphosphonate |

However, there is an additional group of organophosphorus insecticides that have melting points within the temperature range within which the formulation would normally be applied and/or stored. Examples of those organophosphorus insecticides include those compounds shown in Table 2 below:

TABLE 2

| Common Name | Chemical Name | Melting Point ° C. |
| --- | --- | --- |
| Fenitrothion | O,O-dimethyl O-4-nitro-m-tolyl phosphorothioate | 3.4° |
| Fenthion | O,O-dimethyl-O-[4-(methylthio)-m-tolyl] phosphorothioate | 7.5° |
| Fonofos | O-ethyl S-phenyl ethylphosphonothiolothionate | 32° |
| Isofenphos | 1-methylethyl 2-((ethoxy((1-methylethyl)amino)phosphinothioyl)oxy)benzoate | −12° |
| Pirimiphos-ethyl | O-(2-diethylamino)-6-methyl-4-pyrimidinyl) O,O-diethyl phosphorothioate | 15°–18° |

The preferred nominally solid organophosphorus insecticide for use in the present invention is chlorpyrifos. Chlorpyrifos has a melting point of between 42° and 43.5° C.

Solid carriers for organophosphorus insecticides are well known in the art and are useful in the present invention. Solid carriers that can be used in preparing the formulations of the present invention include kaolin clays, such as Kaolinite, dickite, nacrite, anauxite, halloysite, endellite and barden clay; montmorillonite clays, such as, beidellite, nontromite, montmorillonite, hectorite, saponite, savconite and bentonite; attapulgite clays, such as fuller's earth, attapulgite and sepiolite; diatomaceous earths, such as diatomite and kieselguhr; and vermiculite, such as biotite; and synthetic silicates, such as Micro-cel and Silene EF, and various talcs. It is preferred that the solid carriers used in the present invention be in a granular form suitable for agricultural application. It is particularly preferred that the solid carriers used in the present invention are clay carriers; especially, clay carriers selected from kaolin clays, montmorillonite clays and attapulgite clays.

In accordance with the present invention, it has been found that a minor amount of a stabilizer compound selected from cyclohexanone and N-methylpyrrolidone when combined with the solid carrier and organophosphorus insecticide provides a desired level of cold storage stability such that agglomeration or clumping of the cold formulation is reduced or avoided.

The formulation of the present invention is prepared by applying the nominally solid organophosphorus insecticide and the stabilizer compound to the solid carrier, either as a mixture or separately. If applied separately, they can be applied in any order of addition; however, it is preferred that the stabilizer compound be applied first. However, it is preferred in the present invention that the organophosphorus insecticide and the stabilizer compound be applied to the solid carrier as a mixture. The organophosphorus insecticide and the stabilizer compound can be applied to the solid carrier by any means know to those skilled in the art; however, it is preferred that they be applied by spraying.

Some nominally solid organophosphorus insecticides are solids at room or ambient temperature. It is an essential feature of the present invention that the nominally solid organophosphorus insecticide be applied to the solid carrier in liquid form. Therefore, for those nominally solid organophosphorus insecticides that are solid at room or ambient temperatures, they must be heated to their melting point. For example, chlorpyrifos is a solid at room temperature, with a melting point of approximately 42° C. and a boiling point of approximately 200° C. Therefore, the chlorpyrifos must be heated to a temperature between approximately 42° and 200° C.; preferably, between approximately 50° and 60° C. For other nominally solid organophosphorus insecticides that are solid at room or ambient temperatures, the insecticide must be heated to a temperature above its melting point, but well below its boiling point so that evaporation of the active insecticide is held to a minimum.

For those nominally solid organophosphorus insecticides that are liquid at room or ambient temperatures, the insecticide does not need to be heated prior to application to the solid carrier. For those nominally solid organophosphorus insecticides that have melting points near room or ambient temperatures, such that the insecticides are relatively thick, viscous liquids, slight heating may be required to reduce the viscosity of the insecticide before application to the solid carrier, particularly if the insecticide is to be applied to the solid carrier by spraying.

When it is necessary to heat the nominally solid organophosphorus insecticide, the stabilizer compound should also be heated if the stabilizer compound and the insecticides are to be applied to the solid carrier together. It is preferred that the nominally solid organophosphorus insecticide and the stabilizer compound be applied to the solid carrier as a mixture. Therefore, it is desirable to first melt the nominally solid organophosphorus insecticide and then add the stabilizer compound while maintaining the temperature of the mixture above the melting point of the insecticide. The mixture should therefore be maintained at a temperature between the melting point and the boiling point of the nominally solid organophosphorus insecticide. In the case of chlorpyrifos, the mixture should be maintained at a temperature between approximately 42° and 200° C.; preferably, between approximately 50° and 60° C. The mixture should then be agitated or mixed until well blended. The liquid mixture of insecticide and stabilizer compound is then ready for application to the solid carrier.

When the nominally solid organophosphorus insecticide is solid at room or ambient temperatures, i.e., the ambient temperature at which the insecticide is to be applied to the solid carrier, in addition to heating the insecticide, it is necessary to heat the solid carrier to a temperature between the melting point of the insecticide and the boiling point of the insecticide ; i.e., generally between approximately 30° and 300° C. Heating the solid carrier prevents the insecticide from freezing on the surface of the solid carrier when the insecticide contacts the carrier. Heating also facilitates penetration of the nominally solid organophosphorus insecticide and stabilizer compound into the solid carrier. For example, for chlorpyrifos, the solid carrier should be heated to a temperature between approximately 42° and 200° C.; preferably, between approximately 65° and 75° C. The solid carrier can be preheated using any suitable means to obtain the specified temperature. Heating can be accomplished with a jacketed blender, steam coils, contact heaters or fluidized beds.

When the nominally solid organophosphorus insecticide is liquid at room or ambient temperatures, heating of the solid carrier prior to application of the stabilizer compound may not be required.

Any suitable means known to those skilled in the art can be used to apply the nominally solid organophosphorus insecticide and stabilizer compound to the carrier and to mix the materials together. A commonly used device is a tumbling-type mixer made by Munson Machinery Company. Generally, the clay is weighed, preheated and charged to the blender. The insecticide/stabilizer mixture is then sprayed onto the clay using a spray nozzle inside the blender to evenly distribute the liquid onto the clay. Blending of the clay is continued after completion of the liquid addition until a uniform mixture is obtained.

The following examples are illustrative of the present invention and are not intended to limit the scope of the invention as set forth in the appended claims. All temperatures are in degrees Celsius and all percentages are by weight unless specifically stated otherwise.

EXAMPLE 1

The formulation shown in Table 3 below was prepared:

TABLE 3

| Ingredient | Wt. % of Ultimate Formulation | Weight (lbs) |
|---|---|---|
| Agsorb LVM 24/48 clay granules* | 80.0 | 8,000 |
| chlorpyrifos technical (98%) | 15.5 | 1,550 |
| cyclohexanone | 4.5 | 450 |
| TOTAL | 100.0 | 10,000 |

*Agsorb LVM 24/48 clay granules are montmorillonite clay granules available from Oil-Dri Corporation of America of Chicago, Illinois.

The Agsorb granules were weighted and then heated to a temperature of between 65° and 71° C. The heated solid carrier granules were then transferred to a Munson blender. Technical chlorpyrifos (98% by weight) was melted by storing the technical material in a water bath at 50°–55° C. The melted technical material was then pumped into a mixing tank equipped with an agitator and a hot water jacket to maintain the contents of the tank at a temperature of 50°–55° C. Cyclohexanone was added to the mixing tank and agitated until well mixed. The blender was started and the chlorpyrifos/cyclohexanone mixture was sprayed under a pressure of 30 psi onto the surface of the tumbling clay. Two fan-type spray nozzles were used to atomize the chlorpyrifos/cyclohexanone mixture. Spraying time was 8 minutes. Blending continued for another 10 minutes after spraying of the chlorpyrifos/cyclohexanone mixture was completed. The product was transferred from the blender into a packaging hopper where it was then packed in plastic bags that held 50 pounds of the chlorpyrifos/cyclohexanone/clay formulation.

EXAMPLE 2

The formulation shown in Table 4 below was prepared in accordance with the procedure described above in Example 1:

TABLE 4

| Ingredient | Wt. % of Ultimate Formulation | Weight (lbs) |
|---|---|---|
| Agsorb LVM 24/48 clay granules | 82.0 | 8,200 |
| chlorpyrifos technical (98%) | 15.5 | 1,550 |
| cyclohexanone | 2.5 | 250 |
| TOTAL | 100.0 | 10,000 |

The chlorpyrifos/cyclohexanone/clay formulation was also packaged in plastic bags containing 50-pound of the formulation.

EXAMPLE 3

The formulation shown in Table 5 below was prepared in accordance with the procedure described above in Example 1, except that dipropylene glycol was substituted for cyclohexanone:

TABLE 5

| Ingredient | Wt. % of Ultimate Formulation | Weight (lbs) |
|---|---|---|
| Agsorb LVM 24/48 clay granules | 80.0 | 8,200 |
| chlorpyrifos technical (98%) | 15.5 | 1,550 |
| dipropylene glycol | 4.5 | 450 |
| TOTAL | 100.0 | 10,000 |

The chlorpyrifos/dipropylene glycol/clay formulation was also packaged in plastic bags containing 50-pounds of the formulation.

EXAMPLE 4

The formulation shown in Table 6 below was prepared in accordance with the procedure described above in Example 1, except that N-methylpyrrolidone was substituted for cyclohexanone:

TABLE 6

| Ingredient | Wt. % of Ultimate Formulation | Weight (lbs) |
|---|---|---|
| Agsorb LVM 24/48 clay granules | 80.0 | 8,200 |
| chlorpyrifos technical (98%) | 15.5 | 1,550 |
| N-methylpyrrolidone | 4.5 | 450 |
| TOTAL | 100.0 | 10,000 |

The chlorpyrifos/dipropylene glycol/clay formulation was also packaged in plastic bags containing 50-pound of the formulation.

EXAMPLE 5

A refrigerated storage chamber was constructed for evaluating cold stability of test batches of the chlorpyrifos 15% granular insecticide formulations prepared in Examples 1–4 above. The chamber was large enough to store full pallets of product. Fifty-pound bags from each of the four test batches and 50 pound bags of Lorsban 15G manufactured by Dow Agrosciences of Indianapolis, Ind., were stacked in an alternating pattern to make up composite test pallets. Each pallet contained a total of 2,500 pounds of the four test formulations and Lorsban 15G; i.e., 10 bags of each of the four test formulations and 10 bags of Lorsban 15G. The composite pallets were transferred to the cold storage chamber with another full pallet containing 2,500 pounds placed on top of the test pallet to provide a compacting force during storage. At the intervals listed in Table 7 below, a test pallet was removed from cold storage and the bags were opened and evaluated by pouring the contents across a mesh screen with ¼ inch openings. Temperature probes were installed in the cold storage chamber and probes were inserted into bags on the test pallets. On days 2 and 3, the bag temperatures were between 27° and 36° F. (−2.8° and 2.2° C.). For the 7 and 14 day evaluation, the bag temperatures were between 10° and 21° F. (−12.2° and −6.1° C.).

Product aggregation or clumping was determined by estimating the lumber of lumps observed while emptying each bag across the screen and noting whether the lumps were hard or soft. Soft lumps would either break apart by contact with the screen or by gentle movement of the screen. Hard lumps were not broken up by contact with or movement of the screen. The cold storage results are shown in Table 7 below.

TABLE 7

| Days in Storage | Example 1 | Example 2 | Example 3 | Example 4 | Lorsban 15G |
|---|---|---|---|---|---|
| 2 | 0 | 1 soft | >20 hard | 0 | 10 soft |
| 3 | 0 | 1 soft | >20 hard | 0 | 6 soft |
| 7 | 5 soft | 1 soft | >20 hard | 0 | >20 hard |
| 14 | 5 soft | 3 soft | >20 hard | 0 | >20 hard |

The test data shows that the materials made in accordance with the present invention using cyclohexanone and N-methylpyrrolidone; i.e., Examples 1, 2 and 4, had significantly better cold storage stability than either the product made using propylene glycol; i.e., Example 3, or the commercial product Lorsban 15G.

It should be understood, of course, that the foregoing relates only to certain disclosed embodiments of the present invention and that numerous modifications or alterations may be made therein without departing from the spirit and scope of the invention as set forth in the appended claims.

What is claimed is:

1. In a solid cold stabilized insecticidal formulation that comprises from about 2% to about 40% by weight of a nominally solid organophosphorus insecticide, a solid granular clay carrier therefor, and a cold stabilizing amount of a stabilizer compound for said formulation, the improvement in said formulation which comprises using as the stabilizer compound, from about 0.5% to about 10% by weight of the ultimate formulation of a compound selected from cyclohexanone and N-methylpyrrolidone.

2. A composition comprising a solid carrier to which has been applied a mixture, said mixture comprising between approximately 2% and 40% by weight of the ultimate composition of a nominally solid organophosphorus insecticide and between approximately 0.5% and 10% by weight of a stabilizer compound selected from cyclohexanone and N-methylpyrrolidone.

3. The composition of claim 2, wherein said solid carrier is selected from kaolin clays, montmorillonite clays, attapulgite clays, diatomaceous earths, vermiculites, synthetic silicates, and talcs.

4. The composition of claim 2, wherein said stabilizer compound is present in an amount between approximately 2% and 5% by weight of the ultimate composition.

5. The composition of claim 2, wherein said organophosphorus insecticide is chlorpyrifos.

6. The composition of claim 2, wherein said organophosphorus insecticide is selected from Acephate, Bromophos, Chlorpyrifos, Disulfoton, EPN, Fenamiphos, Fenchlorophos, Quinalphos, Trichlorfon, Fenitrothion, Fenthion, Fonofos, Isofenphos, and Pirimiphos-Ethyl.

7. A composition comprising a solid granular clay carrier to which has been applied between approximately 10% and 20% by weight of the ultimate composition chlorpyrifos and between approximately 2% and 5% by weight of the ultimate composition of a stabilizer compound selected from cyclohexanone and N-methylpyrrolidone.

8. The composition of claim 7, wherein said stabilizer compound is cyclohexanone.

9. The composition of claim 7, wherein said stabilizer compound is N-methylpyrrolidone.

10. The composition of claim 7, wherein said clay carrier is selected from kaolin clays, montmorillonite clays, and attapulgite clays.

11. The composition of claim 7, wherein said solid carrier is attapulgite.

12. The composition of claim 7, wherein said solid carrier is montmorillonite.

13. A method comprising the steps of:
applying to a solid granular clay carrier between about 2% and about 40% by weight of a nominally solid organophosphorus insecticide in a liquid state and between approximately 0.5% and 10% by weight of a stabilizer compound selected from cyclohexanone and N-methylpyrrolidone, said clay carrier being at a temperature of between approximately 30° and 200° C.;
mixing the organophosphorus insecticide, stabilizer compound and clay carrier to form a substantially uniform mixture; and
permitting said mixture to cool to ambient temperature.

14. The method of claim 13, wherein said clay carrier is selected from kaolin clays, montmorillonite clays, and attapulgite clays.

15. The method of claim 13, wherein said stabilizer is present in an amount from about 2% to about 5% by weight of the ultimate composition.

16. The method of claim 13, wherein said nominally solid organophosphorus insecticide is chlorpyrifos.

17. The method of claim 13, wherein said nominally solid organophosphorus insecticide is selected from the group of Acephate, Bromophos, Chlorpyrifos, Disulfoton, EPN, Fenamiphos, Fenchlorophos, Quinalphos, Trichlorfon, Fenitrothion, Fenthion, Fonofos, Isofenphos, and Pirimiphos-Ethyl.

18. A method comprising mixing with a clay carrier at a temperature of between approximately 30° and 200° C. between approximately 2% and 40% by weight of a nominally solid organophosphorus insecticide in a liquid state and between approximately 0.5% and 10% by weight of a stabilizer compound selected from cyclohexanone and N-methylpyrrolidone.

19. The method of claim 18, wherein said clay carrier is selected from kaolin clays, montmorillonite clays, and attapulgite clays.

20. The method of claim 18, wherein said stabilizer is present in an amount from about 2% to about 5% by weight of the ultimate composition.

21. The method of claim 18, wherein said nominally solid organophosphorus insecticide is chlorpyrifos.

22. The method of claim 18, wherein said nominally solid organophosphorus insecticide is selected from the group of Acephate, Bromophos, Chlorpyrifos, Disulfoton, EPN, Fenamiphos, Fenchlorophos, Quinalphos, Trichlorfon, Fenitrothion, Fenthion, Fonofos, Isofenphos, and Pirimiphos-Ethyl.

23. The method of claim 18, wherein said stabilizer compound is cyclohexanone.

24. The method of claim 18, wherein said stabilizer compound is N-methylpyrrolidone.

25. The method of claim 18, wherein said clay carrier is montmorillonite.

26. The method of claim 18, wherein said clay carrier is attapulgite.

27. A composition comprising a nominally solid organophosphorus insecticide and a stabilizer compound selected from cyclohexanone and N-methylpyrrolidone, the ratio of nominally solid organophosphorus insecticide to stabilizer compound being between approximately 80:1 and 4:1.

28. A method comprising the steps of:

applying to a solid granular clay carrier between about 2% and about 40% by weight of chlorpyrifos in a liquid state and between approximately 0.5% and 10% by weight of a stabilizer compound selected from cyclohexanone and N-methylpyrrolidone, said clay carrier being at a temperature of between approximately 150° and 160° F.;

mixing the chlorpyrifos, stabilizer compound and clay carrier to form a substantially uniform mixture; and permitting said mixture to cool to ambient temperature.

29. A method comprising mixing with a clay carrier at a temperature of between approximately 150° and 160° F. between approximately 2% and 40% by weight of a nominally solid organophosphorus insecticide in a liquid state and between approximately 0.5% and 10% by weight of a stabilizer compound selected from cyclohexanone and N-methylpyrrolidone.

* * * * *